US012611188B2

(12) United States Patent
Kaushal et al.

(10) Patent No.: US 12,611,188 B2
(45) Date of Patent: Apr. 28, 2026

(54) DEFINING PRESET PARAMETER VALUES FOR AN ULTRASOUND IMAGING SYSTEM

(71) Applicant: KONINKLIJKE PHILIPS N.V., Eindhoven (NL)

(72) Inventors: Nitesh Kaushal, Bangalore (IN); Karthick Raja, Bangalore (IN); Kothawala Aliarshad Aameer, Bangalore (IN); Karthik Krishnan, Bangalore (IN); Subhendu Seth, Bangalore (IN); Pallavi Vajinepalli, Bangalore (IN); Earl M. Canfield, New Braunfels, TX (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 9 days.

(21) Appl. No.: 18/689,171

(22) PCT Filed: Sep. 6, 2022

(86) PCT No.: PCT/EP2022/074748
§ 371 (c)(1),
(2) Date: Mar. 5, 2024

(87) PCT Pub. No.: WO2023/036778
PCT Pub. Date: Mar. 16, 2023

(65) Prior Publication Data
US 2024/0366187 A1      Nov. 7, 2024

Related U.S. Application Data

(60) Provisional application No. 63/241,383, filed on Sep. 7, 2021.

(30) Foreign Application Priority Data

Sep. 23, 2021    (EP) ..................................... 21198598

(51) Int. Cl.
*A61B 8/00* (2006.01)

(52) U.S. Cl.
CPC ............ *A61B 8/5207* (2013.01); *A61B 8/467* (2013.01); *A61B 8/565* (2013.01); *A61B 8/58* (2013.01)

(58) Field of Classification Search
None
See application file for complete search history.

(56) References Cited

U.S. PATENT DOCUMENTS 10,049,301 B2    8/2018    Kluckner et al.
2006/0241455 A1    10/2006    Shvarts
(Continued)

FOREIGN PATENT DOCUMENTS

CN        111126609 A        5/2020
WO     2020020770 A1        1/2020

OTHER PUBLICATIONS

H. Lee et al, "Federated Learning for Thyroid Ultrasound Image Analysis to Protect Personal Information: Validation Study in a Real Health Care Environment", JMIR Medical Informatics, vol. 9, No. 5, pp. 1-9, May 2021 (Year: 2021).*
(Continued)

*Primary Examiner* — Nyrobi Celestine

(57)        ABSTRACT

A mechanism for defining a set of preset parameter values for an ultrasound imaging system. Information about local machine-learning models, generated by a plurality of ultrasound imaging systems and updated responsive to operator feedback, is provided to an external server. The external server generates a global machine-learning model based on this information, which is then used to update the local machine-learning model on target ultrasound imaging systems.

20 Claims, 3 Drawing Sheets

(56)     References Cited

U.S. PATENT DOCUMENTS

| | | | |
|---|---|---|---|
| 2016/0283680 A1* | 9/2016 | Deng ..................... | G16H 50/20 |
| 2019/0042981 A1 | 2/2019 | Bendfeldt | |
| 2019/0350564 A1 | 11/2019 | Gajdos et al. | |
| 2021/0121158 A1 | 4/2021 | Tsymbalenko et al. | |
| 2021/0326698 A1* | 10/2021 | Bukharev .............. | G06N 3/063 |
| 2022/0414464 A1* | 12/2022 | Krishnaswamy ...... | G06N 3/047 |

OTHER PUBLICATIONS

International Search Report and Written Opinion for PCT/EP2022/074748; Mailing date: Nov. 22, 2022, 13 pages.

Anonymous, "Federated Learning," Wikipedia, retrieved from https://en.wikipedia.org/w/index.php?title=Federated_learning&oldid=1033895866#cite_note-:3-4, 2021, 11 pages.

Sui, D. et al., "Distantly Supervised Relation Extraction in Federated Settings," arXiv:2008.05049v1, 2020, 10 pages.

Konečný, J. et al., "Federated Optimization: Distributed Machine Learning for On-Device Intelligence," arXiv:1610.02527v1, 2016, 38 pages.

Li, T et al., "Federated optimization in heterogeneous networks," Federated Optimization in Heterogeneous Networks arXiv:1812.06127v5, 2020, 22 pages.

Wesolowski, T. et al., "Keystroke Data Classification for Computer User Profiling and Verification," Computational Collective Intelligence, 2015, pp. 588-597.

Das, R.K. et al., "User Authentication Based on Keystroke Dynamics," IETE Journal of Research, 2014, vol. 60, No. 3, pp. 229-239.

Zhuo, H.H. et al., "Federated Deep Reinforcement Learning," arXiv:1901.08277v3, 2020, 9 pages.

* cited by examiner

DEFINING PRESET PARAMETER VALUES FOR AN ULTRASOUND IMAGING SYSTEM

CROSS-REFERENCE TO PRIOR APPLICATIONS

This application is the U.S. National Phase application under 35 U.S.C. § 371 of International Application No. PCT/EP2022/074748, filed on Sep. 6, 2022, which claims the benefit of U.S. Provisional Patent Application No. 63/241,383, filed Sep. 7, 2021, and European Patent Application No. 21198598.1, filed on Sep. 23, 2021. These applications are hereby incorporated by reference herein.

FIELD OF THE INVENTION

The present invention relates to the field of ultrasound imaging, and in particular, to the defining of preset parameter values for an ultrasound imaging system.

BACKGROUND OF THE INVENTION

Ultrasound imaging (or ultrasonography) techniques have gained considerable interest in the medical field due to their low cost, non-ionizing radiation, high frame rate and inter-active nature thereby providing ease to various clinical procedures. However, an image quality of ultrasound images is highly operator-dependent, as there are a large number of parameters under a user's control that can be manipulated in order to adjust a quality of the image. The "optimal" values for these parameters differs, for instance, depending upon characteristics of the subject, the anatomical appearance of the target anatomical structure, user/operator preference and even location/environment considerations. The practice of tuning or defining these values is commonly labelled knobo-logy, and the parameters may be labelled knobology param-eters.

Typically, an ultrasound imaging system will have one or more sets of preset or pre-programmed parameter values. Each set of preset parameter values may be referred to simply as a "PRESET". Each set of preset parameter values may be designed for a different circumstance with which the ultrasound imaging system is to be used. For instance, a first set of parameters values may be designed for use in imaging a pregnant individual, whereas a second set of parameter values may be designed for use in performing echocardio-grams.

An inexperienced user may prefer to rely upon a set of preset parameter values, e.g. if they are not confident or experienced in adjusting available parameters in order to adjust image quality, i.e. they have a low level of knobology skill or experience.

There is an ongoing desire to improve image quality of ultrasound images produced by an ultrasound imaging sys-tem. In particular, there is a desire to achieve a desired image quality and/or appearance of images produced by ultrasound imaging systems using a set of preset parameter values.

SUMMARY OF THE INVENTION

The invention is defined by the claims.

According to examples in accordance with an aspect of the invention, there is provided a computer-implemented method for defining a set of preset parameter values at a target ultrasound imaging system.

The computer-implemented method comprises: provid-ing, from the target ultrasound imaging system to an external server, local modelling data that defines a local machine-learning model used by said target ultrasound imaging system to generate a set of preset parameter values for said ultrasound imaging system; receiving, at the target ultra-sound imaging system, global modelling data that defines a global machine-learning model generated by the external server using modelling data of machine-learning models obtained from a plurality of ultrasound imaging systems, including at least the local modelling data; updating, at the target ultrasound imaging system, the local machine-learn-ing model using the global modelling data; and generating, at the target ultrasound imaging system, the set of preset parameter values for said target ultrasound image system using the updated local machine-learning model; generating and/or updating, at the target ultrasound imaging system, the local machine-learning model, to be provided to the external server, responsive to operator feedback at the target ultra-sound imaging system. The set of present parameter values are known as being used to produce ultrasound images at the target ultrasound imaging system.

The present disclosure employs a federated learning approach for training a machine-learning model that defines one or more PRESETs (i.e. sets of preset parameter values) for an ultrasound imaging system. In particular, local machine-learning models (generated by each ultrasound imaging system) are passed to an external server, which combines the obtained local methods in order to generate a global machine-learning model. This global machine-learn-ing model is then pushed or provided to each ultrasound imaging system for use.

It has previously been explained how parameter values define image characteristics of an ultrasound image pro-duced by an ultrasound imaging system, e.g. contrast, graini-ness, noise levels, image quality, image clarity, and so on. Manual setting and adjustment of these parameter values is a time consuming and non-intuitive task, requiring experi-ence and expertise to perform accurately (i.e. to achieve a desired image quality or other characteristic)

Conventionally, the industry PRESETs deployment strat-egy is an open loop, without any scope of obtaining feed-back and refining it further. Moreover, each ultrasound machine is behaving in a passive way with its operator, without adapting (thus predicting) to the changes done on it. The proposed approach provides an automated, closed-loop mechanism for generating or updating preset parameter values for the target ultrasound imaging system. Automatic generation and update of preset parameter values responsive to operator feedback will reduce or completely mitigate a time a practitioner or operator requires to operator-adjust-able settings to achieve desired image characteristics. Pro-posed approaches also enables the possibility of personal-izing or tailoring image appearance, such as for different imaging centers, region-specific practice guidelines, differ-ent populations and regional markets, and/or different fla-vour or habitus of the users. Proposed approaches also provide desired preset values for any ultrasound imaging system even if it is less used or used by inexperienced practitioners, in particular, allowing the collating or com-bining of models more trained or trained using expert practitioners into a single global model that would provide desired preset values.

Moreover, the proposed approach of collating or combin-ing local models into a global model (which is then pushed to each ultrasound system) standardizes images produced using such models. This can improve a reliability and robustness of any AI processing of produced ultrasound images, as the characteristics of the ultrasound image can be standardized (reducing variation in possible inputs to the AI processing, improving its reliability).

In some examples, the step of generating the set of preset parameter values comprises: further training the updated local machine-learning model at the target ultrasound imaging system responsive to operator feedback at the target ultrasound imaging system; and generating, at the target ultrasound imaging system, a set of preset parameter values for said target ultrasound image system using the further trained local machine-learning model.

This approach facilitates the use of experience and expertise of an operator to improve the training and/or learning of the local machine-learning model, e.g. to more quickly train the machine-learning model and/or adapt the local machine-learning model to local conditions and/or environments. This approach facilitates a mechanism by which expertise can be distributed to different ultrasound imaging systems, as expertise of the operator will be used to train the local machine-learning model, which is then passed back in the generation of the global machine-learning model in the external server.

The operator feedback may comprise correction information indicating a correction to a recommended set of preset parameter values for the target ultrasound imaging system generated using the local machine-learning model and/or the updated local machine-learning model.

In some examples, the step of providing modelling data comprises providing, from the target ultrasound imaging system to the external server, experience data indicating an experience of the operator of the target ultrasound imaging system; and the global machine-learning model is generated by a process that includes weighting the modelling data responsive to the experience level of the operator of the target ultrasound imaging system indicated in the experience data.

In this way, more experienced operators contribute a greater amount to the global machine-learning model than other operators. This ensures that local machine-learning models (which are defined by the global modeling data) are more reflective of experienced operators, and therefore provide more appropriate ultrasound images for assessing the condition of the subject. This improves an appearance of the ultrasound image, thereby reducing a likelihood of misdiagnosis or mis-assessment.

In some examples, the local machine-learning model and the global machine-learning model are configured to: receive, as input, information about the target ultrasound imaging system, a subject to be imaged using the target ultrasound imaging system and/or one or more ultrasound images captured by the target ultrasound imaging system; and provide, as output, a set of preset parameter values for the target ultrasound imaging system.

In at least one example, each local machine-learning model is generated and/or updated by performing an iterative process comprising: processing information about the ultrasound imaging system and/or one or more ultrasound images captured by the ultrasound image using the local machine-learning model to generate a set of preset parameter values for the ultrasound imaging system; generating an ultrasound image using the ultrasound imaging system having the set of preset parameter values; determining an image quality of the ultrasound image; and modifying the local machine-learning model based on the determined image quality.

This iterative process may be performed in addition to, alongside and/or as part of a process that generates/updates the local machine-learning model responsive to a user feedback. For instance, the operator feedback may be operator feedback that provides or determines the image quality of the ultrasound image. As another example, the image quality may be an automated determination of image quality, and operator feedback may include differences to preference to the automated determination of image quality. Thus, the local machine-learning model may be initially trained using an automated approach, and then personalized using operator feedback.

There is also proposed a computer-implemented method for defining a local machine-learning model usable to define a set of preset parameter values for one or more target ultrasound imaging systems.

The computer-implemented method comprises: obtaining, at an external server, local modelling data from each of a plurality of ultrasound imaging systems, the local modelling data defining a local machine-learning model used by said ultrasound imaging system to generate a set of preset parameter values for said ultrasound imaging system, the local machine-learning model being generated and/or updated responsive to operator feedback at the target ultrasound imaging system; processing, at the external server, the local modelling data from each ultrasound imaging system to generate a global machine-learning model; and providing global modelling data, defining the global machine-learning model, to each target ultrasound imaging system, wherein each target ultrasound image updates or defines its local machine-learning model responsive to the global modelling data.

This method complements the previously described method performed using the target ultrasound image. The proposed approach facilitates federated learning for defining or updating local machine-learning models used by target ultrasound imaging system using a plurality of other local models of other ultrasound imaging systems. In this way, a collaborative global machine-learning model can be employed.

The proposed approach makes use of local machine-learning models to train the global model. This avoids the need to send large amounts of data to the external server (e.g. if training data were instead sent to the external server), and effectively provides a distributed approach for generating the global machine-learning model. This improves a processing efficiency for generating the global model.

In at least one example, the step of obtaining local modelling data from each ultrasound imaging system comprises obtaining, for each instance of local modelling data, corresponding experience data indicating an experience of the operator of the ultrasound imaging system that provided the local modelling data; and the step of processing, at the external server, the local modelling data from each ultrasound imaging system comprises weighting each instance of local modelling data responsive to the experience level of the operator of the ultrasound imaging system indicated in the corresponding experience data.

Thus, more experienced operators influence the generation of the global model more than inexperienced operators. This makes the global model less susceptible to incorrect or inappropriate feedback from inexperienced operators, which could otherwise lead to less appropriate PRESETs for target ultrasound imaging systems.

In at least one embodiment, the step of obtaining local modelling data from each ultrasound imaging system comprises obtaining, for each instance of local modelling data, corresponding preference data indicating a preference of the operator of the ultrasound imaging system for a style of ultrasound image; and the step of processing, at the external server, the local modelling data from each ultrasound imaging system comprises weighting each instance of modelling responsive to the preference of the operator of the ultrasound imaging system indicated in the corresponding preference data.

In this way, the proposed method is able to generate preference-specific or tailored global machine-learning models, and thereby provide preference-specific local machine-learning models.

In some examples, the one or more target ultrasound imaging systems comprises a plurality of target ultrasound imaging systems; and the plurality of ultrasound imaging systems comprises the plurality of target ultrasound imaging systems. Optionally, the plurality of ultrasound imaging systems comprises only the plurality of target ultrasound imaging systems (i.e. and no others).

Of course, in some examples, the target ultrasound imaging system(s) may comprise ultrasound imaging systems that do not contribute local modelling data for the generation of the global machine-learning model. This approach facilitates provision of an (updated) machine-learning model to new or rarely used ultrasound imaging systems, e.g. during initial set-up of the ultrasound imaging system. In this way, feedback from operators can be used to define (dynamic) PRESETs for ultrasound imaging systems.

There is also proposed a computer implemented method of defining a set of preset parameter values for one or more target ultrasound imaging systems. The computer-implemented method comprises: controlling one or more target ultrasound systems to perform any previously described approach performed by a target ultrasound system; and controlling an external server to perform any previously described method performed by an external server.

Embodiments also provide a computer program product comprising computer program code means which, when executed on a computing device having a processing system, cause the processing system to perform all of the steps of any herein described method.

There is also proposed a target ultrasound system for defining a set of preset parameter values. The target ultrasound system is configured to: provide, to an external server, local modelling data that defines a local machine-learning model used by said target ultrasound imaging system to generate a set of preset parameter values for said ultrasound imaging system; receive, from the external server, global modelling data that defines a global machine-learning model generated by the external server using modelling data of machine-learning models obtained from a plurality of ultrasound imaging systems, including at least the local modelling data; update the local machine-learning model using the global modelling data; generate the set of preset parameter values for said target ultrasound image system using the updated local machine-learning model; and generating and/or updating, at the target ultrasound imaging system, the local machine-learning model, to be provided to the external server, responsive to operator feedback at the target ultrasound imaging system.

There is also proposed an external server for defining a local machine-learning model at one or more target ultrasound imaging systems usable to define a set of preset parameter values. The external server is configured to: obtain local modelling data from each of a plurality of ultrasound imaging systems, the local modelling data defining a local machine-learning model used by said ultrasound imaging system to generate a set of preset parameter values for said ultrasound imaging system, the local machine-learning model being generated and/or updated responsive to operator feedback at the target ultrasound imaging system; process the local modelling data from each ultrasound imaging system to generate a global machine-learning model; and provide global modelling data, defining the global machine-learning model, to each target ultrasound imaging system, wherein each target ultrasound image updates or defines its local machine-learning model responsive to the global modelling data.

The skilled person would be readily capable of modifying the target ultrasound imaging system and/or the external server to carry out any method or process herein described, and vice versa.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
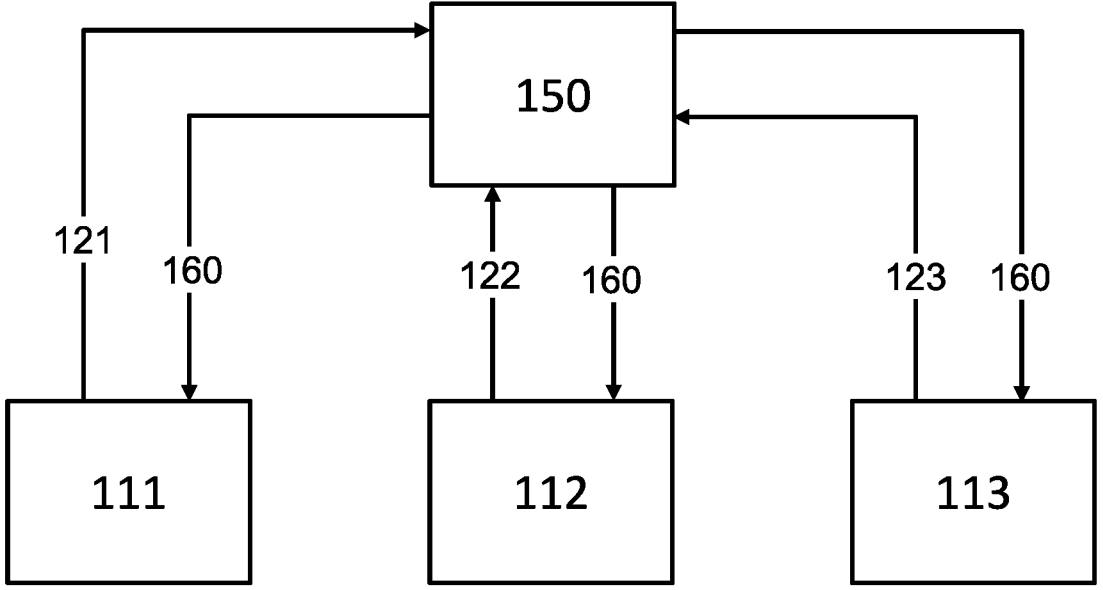
FIG. 1 conceptually illustrates an approach adopted by the disclosure.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a mechanism for defining a set of preset parameter values for an ultrasound imaging system. Information about local machine-learning models, generated by a plurality of ultrasound imaging systems is provided to an external server. The external server generates a global machine-learning model based on this information, which is then used to update the local machine-learning model on target ultrasound imaging systems.

Concepts are based on the realization that implementing a federal learning system into the approach used to define the machine-learning model used by an ultrasound imaging system to define preset parameters provides an improved and more operator appropriate mechanism for defining the machine-learning model. In particular, this approach enriches and standardizes image quality across different target ultrasound imaging systems.

Embodiments can be employed in any suitable ultrasound imaging system environment, such as those used in clinical healthcare, archeology, product testing and so on.

FIG. 1 conceptually illustrates an approach adopted by the present disclosure.

A plurality of ultrasound imaging systems 111, 112, 113 are configured to each generate a local machine-learning model that is used to define a set of preset parameter values for the respective ultrasound imaging system. The set of preset parameter values may define present values for one or more parameters/settings of the ultrasound imaging system, preferably including at least operator-controllable parameters or settings.

Examples of suitable settings for an ultrasound imaging system include a focal position, power output, frequency of output ultrasound, duration of an ultrasound pulse, width of an ultrasound beam, (amplitude of) gain, time gain compensation, contrast, intensity, color, and so on. Various other examples of suitable settings would be apparent to the skilled person familiar with ultrasound imaging systems.

A local machine-learning model is configured to receive, as input, information about the ultrasound imaging system, the subject to be imaged, the operator of the ultrasound imaging system, and/or one or more ultrasound images captured by the ultrasound imaging system; and provide, as output, a set of preset parameter values for the ultrasound imaging system.

Generation, training and/or updating of the local machine-learning model may take place using a conventional machine-learning model training process. In one example, a reinforcement-learning based framework is used to generate and/or update the local machine-learning model based on the activities of the operator (of the ultrasound imaging system) for achieving a particular level of image quality or particular image style. A more complete description of a suitable example of this process will be described later.

Local modelling data 121-123 that defines each local machine-learning model is then passed to an external server 150. The external server 150 is external (i.e. separate) to any of the ultrasound imaging systems, and may be otherwise labelled a central server or federated server. Each ultrasound imaging system 111, 112, 113 provides its own instance 121, 122, 123 of local modelling data that defines the local machine-learning model running or defined by the ultrasound imaging system. An instance of local modelling data may contain a local machine-learning model or may contain data that otherwise defines the local machine-learning model, e.g. values for weights of the local machine-learning model or gradients for the local machine-learning model.

Each instance of local modelling data 121, 122, 123 is then processed or combined (e.g. merged) by the external server to generate a global machine-learning model. In this way, the local models may effectively be statistically merged to form a consolidated or global model.

Global modelling data 160, defining the global machine-learning model, may then be provided to one or more target ultrasound imaging systems, e.g. the ultrasound imaging systems 111, 112, 113. The global modelling data may provide the same form of information about the global machine-learning model as the local modeling data provides about a local machine-learning model.

The global modelling data is then used, by the target ultrasound imaging system(s), to define or update the local machine-learning model used by said target ultrasound imaging system.

In this way, a federated learning scheme is usable to define the local machine-learning model used by a target ultrasound imaging system to generate a set of preset/predefined parameter values.

In some examples, each instance of local modelling data may (when combined by the external server) be weighted. This means that some instances of local modelling data may influence the global machine-learning model to a greater or lesser extent than other instances of local modelling data. A greater weighting of the local modelling data means a greater influence on the global machine-learning model.

In particular examples, more weighting may be given to instances of local modelling data that represent local machine-learning models trained using feedback from a more experienced operator. Thus, an experience level of an operator may influence a weighting of the local modelling data when combined to generate the global machine-learning model.

In this way, each ultrasound imaging system 111-113 may be configured to provide (alongside local modelling data) corresponding experience data. The experience data may indicate an experience of the operator of the ultrasound imaging system that provided the local modelling data. Processing, at the external server 150, the local modelling data from each ultrasound imaging system may similarly comprise weighting each instance of local modelling data responsive to the experience level of the operator of the ultrasound imaging system indicated in the corresponding experience data.

The experience data may comprise a measure or other indicator of an experience level of the ultrasound imaging system. An experience level can be determined, for instance, based on a number of interactions between the operator and the ultrasound imaging system (e.g. where more interactions indicates a greater familiarity with the ultrasound imaging system). As another example, an experience level may be determined based on information about the operator of the ultrasound imaging system, e.g. a job role (e.g. a senior technician will be more experienced than a junior technician), a number of subjects under the responsibility of the operator (more subjects indicating a greater experience level) and/or a number of years in the profession (more years indicating a greater level of experience).

Thus, experience data may be generated by processing information about the operator and/or an operator's interactions with the ultrasound imaging system to generate a measure of predicted experience level.

In some examples, a global machine-learning model may be configured or designed for a particular/target operator preference. It is herein recognized that different operators prefer different appearances for an ultrasound image, e.g. some prefer a grainier appearance for an ultrasound image, whereas others prefer a smoother appearance. This preference may be cultural, based on past experience and/or (medical) specialty. The appearance of an ultrasound image is dependent upon the parameter values of the ultrasound imaging system that generates the ultrasound image.

In some examples, more weighting may be given to instances of local modelling data that represent local machine-learning models trained using feedback from operators having a predetermined preference (for ultrasound images).

Thus, each ultrasound imaging system may be configured to provide (alongside local modelling data) corresponding preference data. The preference data may indicate a preference of the operator of the ultrasound imaging system that provided the local modelling data regarding the style, appearance or type of ultrasound image produced by the local modelling data. Processing, at the external server, the local modelling data from each ultrasound imaging system may similarly comprise weighting each instance of local modelling data responsive to the preference of the operator of the ultrasound imaging system indicated in the corresponding experience data.

In this way, the global machine-learning model may be designed or configured for a particular type of preference for an operator. Of course, multiple global machine-learning models could be generated (e.g. for different target preferences), each global machine-learning model assigning a different weighting depending upon the target preference. In this way, multiple versions of the global machine-learning model may be generated, each version for a difference operator preference or the like.

The global modelling data 160 provided to or obtained by the target ultrasound imaging system may be responsive to a preference of the operator of the target ultrasound imaging system 111-113, so that a different version of the global machine-learning model may provide the global modelling data depending upon the preference of the operator.

In some examples, the global machine-learning method may be generated responsive to both a preference and an experience level of the operator associated with each local machine-learning method. For instance, weightings for different local machine-learning methods may be dependent upon both a preference and experience of the operator that provided feedback for training the local machine-learning method. In this way, a global machine-learning method may be trained for a particular type of preference, with greater weighting being given to more experienced operators having that type of preference.

Thus, user profiling may be performed using a two-staged process: categorizing the operators based on their preferences/taste/choice, followed by their experience level given each preference level.

A working example of a suitable method of generating a global machine-learning model is hereafter described.

In this example, the underlying structure of each local machine-learning model and the global machine-learning model is identical, differing only in the value of weights used in the machine-learning model. For instance, each machine-learning model may be a neural network (having a same number of layers, and number of nodes in each layer) in which the value of weighted connections between nodes differs for different models. The modelling data identifies the values of each weight in the local/global model.

In one example, generating the global machine-learning model comprises, for each weight, averaging the received weight values for that weight, to thereby define an average weight value for said weight. The global machine-learning model may thereby effectively be an average of the local machine-learning models.

In another example, generating the global machine-learning model comprises, for each weight, performing a weighted average of the received weight values for that weight, to thereby define a weighted average weight value used in the global model for said weight. The global machine-learning model may thereby effectively be a weighted average of the local machine-learning models.

The weighting may be responsive, for instance, to an experience level of an operator of the ultrasound imaging system that defines the local machine-learning model. In particular, more weight may be given to the local machine-learning models that are associated (i.e. trained with) more experienced operators.

In some embodiments, the weighting may be responsive to a preference of the operator of the ultrasound imaging system. In this way, greater weighting may be given to values for weights of local modelling data representing data generated for a preference that is closer to a target preference for the global machine-learning model.

Of course, the weighting may be responsive to a combination of any of these features or characteristics.

Other approaches for combining weights of different local machine-learning models to generate a global machine-learning model will be apparent to the skilled person. Similarly, other approaches for weighting or biasing weights of different local machine-learning models in the generation of a global machine-learning model will be apparent to the skilled person.

Other approaches for generating a global machine-learning model from information about the local machine-learning models will be apparent to the skilled person, and may be known as federated optimization approaches. Examples of such approaches are known in the art (e.g. FedAvg or FedProx). One example is provided by Konečný, Jakub, et al. "Federated optimization: Distributed machine-learning for on-device intelligence." arXiv preprint arXiv: 1610.02527 (2016). Another example is provided by Li, Tian, et al. "Federated optimization in heterogeneous networks." arXiv preprint arXiv:1812.06127 (2018).

Figure 2:
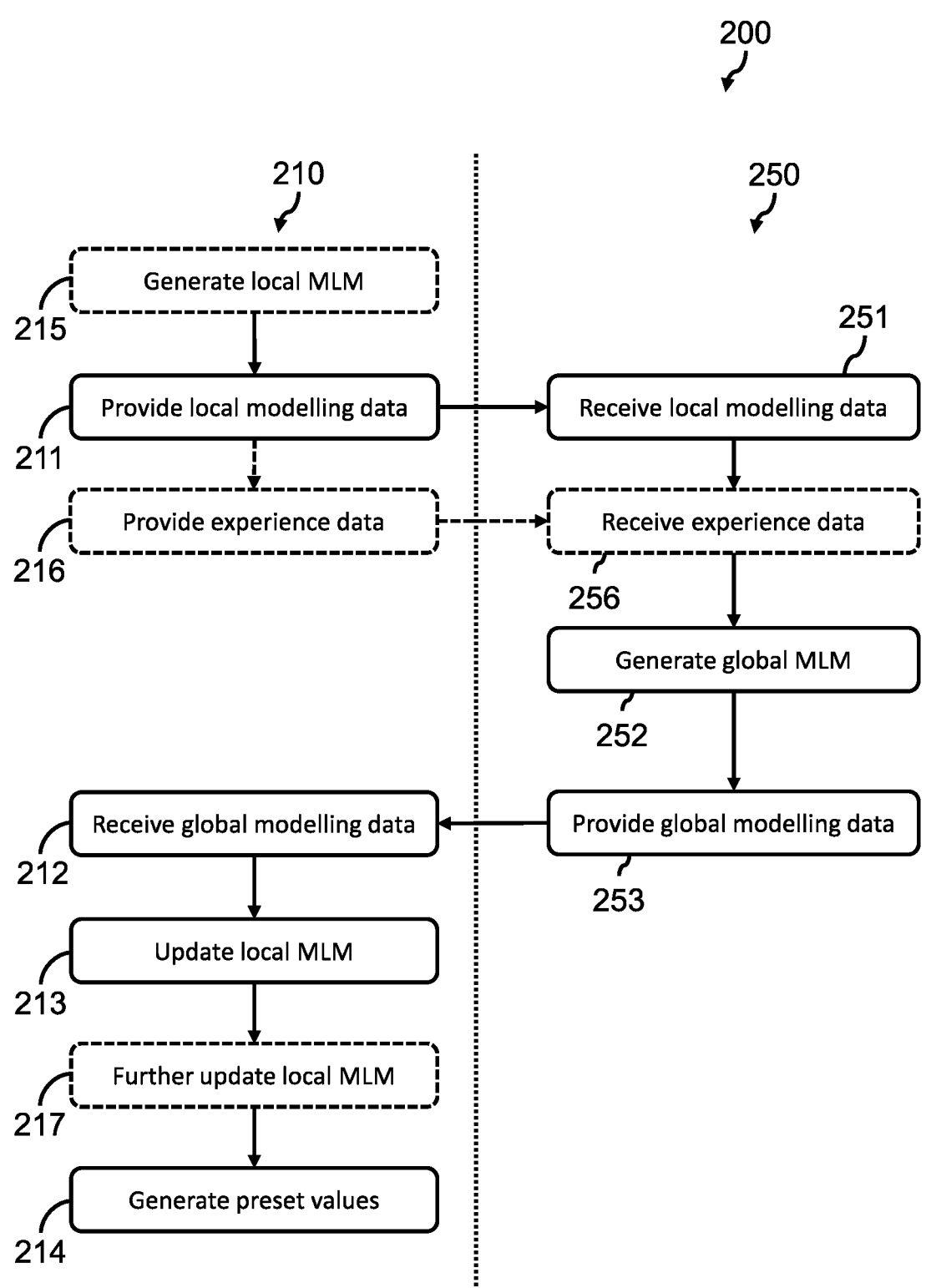
FIG. 2 is a flowchart illustrating a process according to an embodiment.

FIG. 2 illustrates a process 200 according to an embodiment of the invention. The process 200 is formed of two computer-implemented methods 210, 220 that are implemented by a target ultrasound imaging system and an external server respectively.

The process 200 comprises a step 211 of providing, from the target ultrasound imaging system to an external server, local modelling data that defines a local machine-learning model used by said target ultrasound imaging system to generate a set of preset parameter values for said ultrasound imaging system.

The process 200 comprises a corresponding step 251 of obtaining the local modelling data from the target ultrasound imaging system. Step 251 may further obtain local modelling data from one or more other ultrasound imaging systems (not shown).

The process 200 then performs a step 252 of processing, at the external server, the local modelling data from each ultrasound imaging system to generate a global machine-learning model. In this way, a global machine-learning model is generated from the local modelling data. Examples of this process have been previously described.

The process 200 then performs a step 253 of providing global modelling data, defining the global machine-learning model to each target ultrasound imaging system.

Accordingly, in a step 212, the target ultrasound imaging system receives global modelling data that defines a global machine-learning model generated by the external server.

In step 213, the target ultrasound imaging system updates the local machine-learning model using the global modelling data. For instance, where the machine-learning models are identically structured neural networks, and the global modelling data identifies values for weights of the neural network, step 213 may comprise replacing the values of weights of the local machine-learning model with the values of weights defined in the global modelling data.

In step 214, the target ultrasound imaging system generates the set of preset parameter values for said target ultrasound image system using the updated local machine-learning model.

For instance, step 214 may comprise providing the updated local machine-learning model with information about the target ultrasound imaging system with information about the target ultrasound imaging system, a subject to be imaged using the target ultrasound imaging system and/or one or more ultrasound images captured by the target ultrasound imaging system. The updated local machine-learning model may then output a set of preset parameter values for the target ultrasound imaging system.

The process 200 may comprise a step 215 of generating the local machine-learning model, which may comprise defining and training the local machine-learning model. The generation of the local machine-learning model is preferably responsive to operator feedback and/or input (e.g. at an input interface of the target ultrasound imaging system). A more complete example of this process will be described below.

The process 200 may comprise a step 216 of providing, from the target ultrasound imaging system to the external server, experience data indicating an experience level of the operator. In particular, the operator may be an operator who has provided feedback for training the local machine-learning model during its generation in step 215.

Step 216 may comprise determining an experience level of the operator, to thereby define the experience data.

By way of example, step 216 may comprise monitoring a number or pattern of interactions of the operator with the ultrasound imaging system. The fewer interactions with the ultrasound imaging system, the greater the experience level of the operator. This is because an inexperienced operator will require a greater number of interactions with the ultrasound imaging system (e.g. adjusting user-modifiable parameters or the like) to obtain their desired image characteristics. An experienced clinician will be able to more quickly diverge upon their desired image characteristics.

In other words, the improvement of image quality from those captured using default parameters (of the ultrasound imaging system), those captured using operator-modified parameters with fewer, and faster operations/interactions can act as the metric for experience level estimation.

In some examples, complexity of the anatomy under investigation can also be used as a correcting factor of standardization, which can also be measured by quantitative image quality directly/indirectly.

Other approaches make use of keystroke classification in order to detect experience level of operators or to otherwise profile the operators of the ultrasound imaging system. Examples are disclosed by Wesolowski, Tomasz Emanuel, and Piotr Porwik. "Keystroke data classification for computer user profiling and verification." Computational collective intelligence. Springer, Chain, 2015. 588-597 or Das, Rajat Kumar, Sudipta Mukhopadhyay, and Puranjoy Bhattacharya. "User authentication based on keystroke dynamics." IETE Journal of Research 60.3 (2014): 229-239.

In another example, step 216 may comprise processing operator information to determine the experience level. For instance, operators in more senior roles may be considered to have a greater experience level.

The process 200 may comprise a step 256 of obtaining, at the external server, the experience data. The experience data may be used during the generation of the global machine-learning model, e.g. using any previously described approach.

The process 200 may be modified to further comprise determining a preference of the operator of the ultrasound imaging system. Step 252 may be appropriately modified to generate the global model using information about the preference of the operator of the ultrasound imaging system, e.g. to generate a preference-specific global model.

The process 200 may further comprise a step 217 of further updating the local machine-learning model (after it has been updated using the global modelling data). This may be performed, for instance, responsive to operator feedback to the set of parameter values generated by the local machine-learning model and/or an ultrasound image produced by the ultrasound imaging system using the set of parameter values.

It will be appreciated that process 200 may be repeated or iteratively performed, e.g. to provide repeated updates to the global machine-learning model.

A first computer-implemented method 210 according to an embodiment is performed by the target ultrasound imaging system, and comprises steps 211-214. Any of optional steps 215-217 may be incorporated into the first computer-implemented method. Accordingly, there is a proposed a target ultrasound imaging system that is configured to perform the first computer-implemented method.

A second computer-implemented method according to an embodiment is performed by the external server, and comprises steps 251-253. Of course, optional step 256 may be performed by the second computer-implemented method. Accordingly, there is a proposed an external server that is configured to perform the second computer-implemented method.

Figure 3:
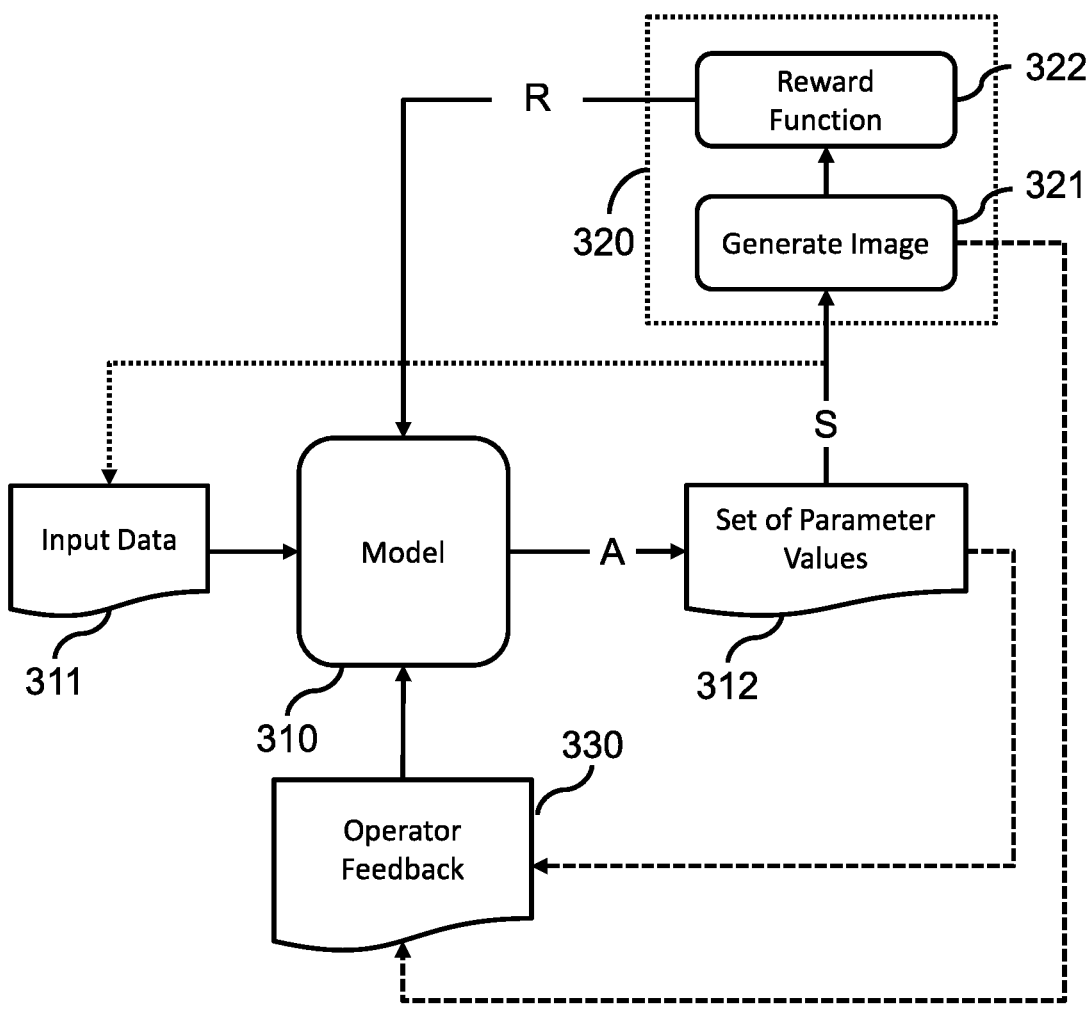
FIG. 3 illustrates an approach for training a local machine-learning model.

FIG. 3 illustrates an approach for generating and/or updating a local machine-learning model 310, which can be employed to perform step 215 and/or step 217 illustrated in FIG. 2. Here, the machine-learning model 310 may comprise a neural network or other form of machine-learning model that can be trained using a reinforcement mechanism.

As previously explained, the purpose of a machine-learning model 310 (hereafter: model for conciseness) is to process input data 311 to define (as output data) a set of preset parameter values for an ultrasound imaging system.

The input data may comprise, for instance, information about the target ultrasound imaging system, a subject to be imaged using the target ultrasound imaging system, an operator of the ultrasound imaging system and/or one or more ultrasound images. By way of example, the input data may comprise one or more features extracted from an ultrasound image and/or current values for the parameters of the ultrasound imaging system. Other suitable examples will be described later in this disclosure.

In a first alternative, the model may directly output a recommended set of preset parameter values for the ultrasound imaging system.

In a second alternative, the model 310 may provide a recommended action A to modify an existing set of preset parameter values. Thus, the machine-learning model may define a recommended action that defines the sets of preset parameter values for the ultrasound imaging system. The hereafter-described embodiment assumes the second alternative is employed by the machine-learning model.

The current set of preset parameter values may be defined as a current state S (i.e. of the preset parameters).

The model 310 learns by interacting with an environment 320. The environment 320 provides automated feedback on the closeness of the set of preset parameter values to a desired outcome. This feedback is in the form of a reward signal R. In the illustrated example, the environment 320 generates, in process 321, an ultrasound image using the set of preset parameter values. A reward function 322 then provides automatic feedback on the closeness of the generated ultrasound image to desired characteristics for the ultrasound image. For instance, the reward function may be an automated image quality determining function, examples of which are known in the art.

The model 310 attempts to learn a policy that maximizes both immediate and subsequent future rewards (the so-called optimal policy). The model may observe the current state (i.e. the current set of preset parameter values) and choose an action to modify the current state, e.g. from a set of possible discrete actions. Each action results in an associated reward defined by the reward signal. This may be a positive reward, a negative reward or null reward, depending on the outcome of the action. For example, positive reward could be an increased image quality. The model will attribute the reward with that of the actions and indirectly on the states (features) observed, at each step.

The actions space consists of a (discrete) number of actions, to be taken on the set of parameters. For example if we have two parameters where the parameter set is simple "ON" and "OFF". We can have four possible action combinations.

If the size of the actions space dimensions is large, then it can be converted to a discrete actions space using some encoding techniques. For example, if there are five parameters to be adjusted with three levels of adjustments, each they can be encoded using binary encoding scheme of four cells. 15 possible actions can be encoded using 24=16 possible combinations. It is possible to encode an action space of 1024 with just 10 binary cells.

The output of the reward function is a proxy for, i.e. representative of the true goal. In some examples, the reward function encourages the model to move towards a parameter set that improves the quality of the ultrasound image. The reward can be discrete R or continuous, and may quantify an improvement or reduction in the image quality. In some examples, the relative image quality of the previous image is compared to that of the current image, which difference can be used as a reward for turning the model.

The final or terminal state is reached when the model is unable to take any further actions that improve the reward signal. In the present case, the terminal or final state may be defined as the state beyond which there is no possibility of improving the image quality by taking any further actions. At this stage, further automated training of the model can be terminated.

In some examples, training may be (e.g. prematurely) terminated if more than a predetermined maximum number of modifications to the model have taken place. This approach helps reduce the likelihood and/or number of times that modifications to the model loop, thereby saving processing power.

In this way, the (local) machine-learning model may be trained using an iterative process. This iterative process may comprise processing information about the ultrasound imaging system and/or one or more ultrasound images captured by the ultrasound image using the local machine-learning model to generate a set of preset parameter values for the ultrasound imaging system; generating an ultrasound image using the ultrasound imaging system having the set of preset parameter values; determining an image quality of the ultrasound image; and modifying the local machine-learning model based on the determined image quality.

It has previously been described how operator feedback 330 may be used in the training of the model. This approach takes advantage of experience and expertise of operators in order to reduce a number of iterations required to converge and/or to tune the model to an operator's desires. The operator feedback may be employed during automated training of the model (e.g. during the process previously described to actively reduce iterations of the training by allowing the operator to respond to the training performance), in advance of automated training (to provide a first benchmark that is likely to reduce a number of iterations performed) and/or following automated training (to tune an automatically generated model to an operator's specific requirements).

The operator feedback may be responsive to an operator's recommended adjustment to an automatically generated set of preset parameter values and/or an operator's recommended set of preset parameter values. This difference may be used to define a desired state to be defined by the model. A backpropagation technique may be used to modify the model based on the desired state to be defined by the model. Backpropagation techniques are well established in the art.

In this way, according to one example, the operator feedback may comprise correction information indicating a correction to a recommended set of preset parameter values for the target ultrasound imaging system generated using the local machine-learning model and/or the updated local machine-learning model. The correction information may be used (e.g. via a backpropagation technique) to update or correct the model.

In another example, the operator feedback may be used to override the reward function, for instance, to label a generated image (in step 321). This information may be used to identify to the model that a particular action or set of parameter values is not optimal. This approach facilitates the use of operator feedback in an automated learning mechanism.

In this way, feedback from an operator is able to influence or define the model.

The operator feedback may be provided via a user interface of the ultrasound imaging system. In order to allow an operator to assess the progress and/or suitability of the model, a user-perceptible output of the ultrasound imaging system (e.g. a display or speaker) may provide user-perceptible information on the current state (i.e. the current set of preset parameter values) and/or an ultrasound image currently produced by the ultrasound imaging system.

As previously described, input data is processed by the model to control or define the set of preset parameter values.

The input data may comprise features from a currently produced ultrasound image (i.e. a current scan) by the ultrasound imaging system. In one example, a convolution neural network can be used to process the ultrasound image to extract features.

The input data may comprise information of the ultrasound imaging system. For instance, the input data may comprise the (current) set of parameter values.

Further examples of suitable input data include examination specific features, i.e. features that depend upon a current purpose for the ultrasound scan input. Examples of such features include an indicator of examination type, a gestational age for obstetric scans, an identification of a target anatomical feature and so on.

Other examples include characteristics of the subject, which may be defined by the operator (e.g. at a user interface to the ultrasound imaging system), such as BMI, age, gender, fat thickness.

Yet another example includes one or more parameters from a real time anatomy identifier, e.g. determined by an anatomy identifier that processes an ultrasound image produced by the ultrasound imaging system. In some instances, an anatomy identifier may provide its own recommended parameter values for the ultrasound system (e.g. recommended depth, placement of focal point etc.), which may be targeted towards particular parts of the anatomy. The model may use these recommended parameter values as part of the input data for defining the set of preset parameter values.

The goal of training the model 310 may be to maximize the discounted cumulative rewards $R_{t0}=\Sigma_{t=0}^{\infty}\gamma^{\{t-t0\}}r_t$, where $r_t$ is the value of the reward signal at time t, and there is a discount function $\gamma^{\{t-t}_0\}}$ The discount $\gamma\in(0,1)$ aims to ensure the cumulative sum of rewards converges. It helps to give importance to the most immediate rewards compared to the future reward.

There is an aim for a model to choose the action that maximizes the reward for a given current state, i.e. identify action π*in which:

$$\pi^* = \mathrm{argmax}_a Q^*(s, a) \qquad (1)$$

where s represents a current state and a represents all possible actions for modifying the current state.

In a conventional q-learning problem, a function Q*: state X action→Reward would be able to indicate the reward for each action (facilitating ease of determining the best action to take). However, the size of the state and/or action space may be too large for efficient processing. It is recognized that a machine-learning model can provide a good approximation for this function Q* with the ability to model complex relationships between states and actions. Accordingly, it is possible to train the model to resemble Q*.

Hence, for a training update, the following equation (based on bellman equation) can be employed:

$$Q^{\pi}(s, a) = r + \gamma Q^{\pi}(s', \pi(s')) \qquad (2)$$

The difference between the two is considered as the temporal difference error and can be calculated as:

$$\delta = Q(s, a) - \left(r + \gamma \max_a Q(s', a)\right). \qquad (3)$$

The model may be configured or controlled to minimize this above-mentioned TD (temporal difference) error using Huber loss. The Huber loss acts like a mean. There are certain advantages in using Huber loss, since it is far more robust in the presence of an outlier. Huber loss (L) is defined as:

$$L = \frac{1}{B}\sum_{(s,a,s',r)\in B}L(\delta) \qquad (4)$$

$$\text{where } L(\delta) = \begin{cases} \frac{1}{2}\delta^2 \text{ for } |\delta| \le 1 \\ |\delta| - \frac{1}{2} \text{ otherwise} \end{cases}, \qquad (5)$$

The skilled person would be readily capable of developing a processor or device for carrying out any herein described method. Thus, each step of the flow chart may represent a different action performed by a processor or device, and may be performed by a respective module of the processor or device.

Embodiments may therefore make use of a processor or device. In particular, any herein described ultrasound imaging system and/or external server may make use of, or be embodied by, such a processor or device.

The processor or device can be implemented in numerous ways, with software and/or hardware, to perform the various functions required. A processor or device is one example of a processor or device that employs one or more microprocessor or devices that may be programmed using software (e.g., microcode) to perform the required functions. A processor or device may however be implemented with or without employing a processor or device, and also may be implemented as a combination of dedicated hardware to perform some functions and a processor or device (e.g., one or more programmed microprocessor or devices and associated circuitry) to perform other functions.

Examples of processor or device components that may be employed in various embodiments of the present disclosure include, but are not limited to, conventional microprocessor or devices, application specific integrated circuits (ASICs), and field-programmable gate arrays (FPGAs).

In various implementations, a processor or device or processor or device may be associated with one or more storage media such as volatile and non-volatile computer memory such as RAM, PROM, EPROM, and EEPROM. The storage media may be encoded with one or more programs that, when executed on one or more processor or devices and/or processor or devices, perform the required functions. Various storage media may be fixed within a processor or device or processor or device or may be transportable, such that the one or more programs stored thereon can be loaded into a processor or device or processor or device.

It will be understood that disclosed methods are preferably computer-implemented methods. As such, there is also proposed the concept of a computer program comprising code means for implementing any described method when said program is run on a processor or device, such as a computer. Thus, different portions, lines or blocks of code of a computer program according to an embodiment may be executed by a processor or device or computer to perform any herein described method. In some alternative implementations, the functions noted in the block diagram(s) or flow chart(s) may occur out of the order noted in the figures. For example, two blocks shown in succession may, in fact, be executed substantially concurrently, or the blocks may sometimes be executed in the reverse order, depending upon the functionality involved.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or device or other unit may fulfill the functions of several items recited in the claims. The mere fact that certain measures are recited in mutually different dependent claims does not indicate that a combination of these measures cannot be used to advantage. If a computer program is discussed above, it may be stored/distributed on a suitable medium, such as an optical storage medium or a solid-state medium supplied together with or as part of other hardware, but may also be distributed in other forms, such as via the Internet or other wired or wireless telecommunication systems. If the term "adapted to" is used in the claims or description, it is noted the term "adapted to" is intended to be equivalent to the term "configured to". Any reference signs in the claims should not be construed as limiting the scope.

The invention claimed is:

1. A computer-implemented method for defining a set of preset parameter values used to produce ultrasound images at a target ultrasound imaging system, the computer-implemented method comprising:

providing, from the target ultrasound imaging system to an external server, local modelling data that defines a local machine-learning model used by said target ultrasound imaging system to generate a set of preset parameter values for said ultrasound imaging system;

receiving, at the target ultrasound imaging system, global modelling data that defines a global machine-learning model generated by the external server using modelling data of machine-learning models obtained from a plurality of ultrasound imaging systems, including at least the local modelling data;

updating, at the target ultrasound imaging system, the local machine-learning model using the global modelling data;

generating, at the target ultrasound imaging system, the set of preset parameter values for said target ultrasound image system using the updated local machine-learning model; and one or more of generating and updating, at the target ultrasound imaging system, the local machine-learning model, to be provided to the external server, responsive to operator feedback at the target ultrasound imaging system.

2. The computer-implemented method of claim 1, wherein the generating the set of preset parameter values comprises:

further training the updated local machine-learning model at the target ultrasound imaging system responsive to operator feedback at the target ultrasound imaging system; and generating, at the target ultrasound imaging system, a set of preset parameter values for said target ultrasound image system using a further trained local machine-learning model.

3. The computer-implemented method of claim 1, wherein the operator feedback comprises correction information indicating a correction to a recommended set of preset parameter values for the target ultrasound imaging system generated using one or more of the local machine-learning model and the updated local machine-learning model.

4. The computer-implemented method of claim 1, wherein:

the providing modelling data comprises providing, from the target ultrasound imaging system to the external server, experience data indicating an experience of the operator of the target ultrasound imaging system; and the global machine-learning model is generated by a process that includes weighting the modelling data responsive to the experience level of the operator of the target ultrasound imaging system indicated in the experience data.

5. The computer-implemented method of claim 1, wherein the local machine-learning model and the global machine-learning model are configured to:

receive, as input, information about the target ultrasound imaging system, a subject to be imaged using one or more of the target ultrasound imaging system and one or more ultrasound images captured by the target ultrasound imaging system; and provide, as output, a set of preset parameter values for the target ultrasound imaging system.

6. The computer-implemented method of claim 1, wherein each local machine-learning model is one or more of generated and updated by performing an iterative process comprising:

processing information about one or more of the ultrasound imaging system and one or more ultrasound images captured by the ultrasound image using the local machine-learning model to generate a set of preset parameter values for the ultrasound imaging system;

generating an ultrasound image using the ultrasound imaging system having the set of preset parameter values;

determining an image quality of the ultrasound image; and modifying the local machine-learning model based on the determined image quality.

7. The computer-implemented method of claim 1, wherein the global modelling data provides the same form of information about the global machine-learning model as the local modeling data provides about a local machine-learning model.

8. A computer-implemented method for defining a local machine-learning model usable to define a set of preset parameter values used to produce ultrasound images at one or more target ultrasound imaging systems, the computer-implemented method comprising:

obtaining, at an external server, local modelling data from each of a plurality of ultrasound imaging systems, the local modelling data defining a local machine-learning model used by said ultrasound imaging system to generate a set of preset parameter values for said ultrasound imaging system, the local machine-learning model being one or more of generated and updated responsive to operator feedback at the target ultrasound imaging system;

processing, at the external server, the local modelling data from each ultrasound imaging system to generate a global machine-learning model; and providing global modelling data, defining the global machine-learning model, to each target ultrasound imaging system, wherein each target ultrasound image updates or defines its local machine-learning model responsive to the global modelling data.

9. The computer-implemented method of claim 8, wherein:

the obtaining local modelling data from each ultrasound imaging system comprises obtaining, for each instance of local modelling data, corresponding experience data indicating an experience of the operator of the ultrasound imaging system that provided the local modelling data; and the processing, at the external server, the local modelling data from each ultrasound imaging system comprises weighting each instance of local modelling data responsive to the experience level of the operator of the ultrasound imaging system indicated in the corresponding experience data.

10. The computer-implemented method of claim 8, wherein:

the obtaining local modelling data from each ultrasound imaging system comprises obtaining, for each instance of local modelling data, corresponding preference data indicating a preference of the operator of the ultrasound imaging system for a style of ultrasound image; and the processing, at the external server, the local modelling data from each ultrasound imaging system comprises weighting each instance of modelling responsive to the preference of the operator of the ultrasound imaging system indicated in the corresponding preference data.

11. The computer-implemented method of claim 7, wherein:

the one or more target ultrasound imaging systems comprises a plurality of target ultrasound imaging systems; and the plurality of ultrasound imaging systems comprises the plurality of target ultrasound imaging systems, and comprises only the plurality of target ultrasound imaging systems.

12. A computer implemented method of defining a set of preset parameter values used to produce ultrasound images at one or more target ultrasound imaging systems, the computer-implemented method comprising:

controlling one or more target ultrasound systems to perform the method of claim 1; and controlling an external server to perform the method of claim 8.

13. A computer program product comprising computer program code means which, when executed on a computing device having a processing system, cause the processing system to perform all of the steps of the method according to claim 1.

14. A target ultrasound system for defining a set of preset parameter values used to produce ultrasound images, the target ultrasound system being configured to:

provide, to an external server, local modelling data that defines a local machine-learning model used by said target ultrasound imaging system to generate a set of preset parameter values for said ultrasound imaging system;

receive, from the external server, global modelling data that defines a global machine-learning model generated by the external server using modelling data of machine-learning models obtained from a plurality of ultrasound imaging systems, including at least the local modelling data;

update the local machine-learning model using the global modelling data;

generate the set of preset parameter values for said target ultrasound image system using the updated local machine-learning model; and one or more of generate and update, at the target ultrasound imaging system, the local machine-learning model, to be provided to the external server, responsive to operator feedback at the target ultrasound imaging system.

15. An external server for defining a local machine-learning model at one or more target ultrasound imaging systems usable to define a set of preset parameter values used to produce ultrasound images, the external server being configured to:

obtain local modelling data from each of a plurality of ultrasound imaging systems, the local modelling data defining a local machine-learning model used by said ultrasound imaging system to generate a set of preset parameter values for said ultrasound imaging system, the local machine-learning model being one or more of generated and updated responsive to operator feedback at the target ultrasound imaging system;

process the local modelling data from each ultrasound imaging system to generate a global machine-learning model; and provide global modelling data, defining the global machine-learning model, to each target ultrasound imaging system, wherein each target ultrasound image updates or defines its local machine-learning model responsive to the global modelling data.

16. The target ultrasound system of claim 14, wherein the effecting the generation the set of preset parameter values, the target ultrasound system is further configured to:

further train the updated local machine-learning model at the target ultrasound imaging system responsive to operator feedback at the target ultrasound imaging system; and generate, at the target ultrasound imaging system, a set of preset parameter values for said target ultrasound image system using the further trained global machine-learning model.

17. The target ultrasound system of claim 14, wherein the operator feedback comprises correction information indicating a correction to a recommended set of preset parameter values for the target ultrasound imaging system generated using one or more of the local machine-learning model and the updated local machine-learning model.

18. The target ultrasound system of claim 14, wherein when providing the modelling data, the system is further configured to:

provide, from the target ultrasound imaging system to the external server, experience data indicating an experience of the operator of the target ultrasound imaging system, wherein the global machine-learning model is generated by a process that includes weighting the modelling data responsive to the experience level of the operator of the target ultrasound imaging system indicated in the experience data.

19. The target ultrasound system of claim 14, wherein the local machine-learning model and the global machine-learning model are configured to:

receive, as input, information about the target ultrasound imaging system, a subject to be imaged using one or more of the target ultrasound imaging system and one or more ultrasound images captured by the target ultrasound imaging system; and provide, as output, a set of preset parameter values for the target ultrasound imaging system.

20. The target ultrasound system of claim 14, wherein when each local machine-learning model is generated and/or updated by performing, the target ultrasound system is further configured iteratively to:

process information about the ultrasound imaging system and/or one or more ultrasound images captured by the ultrasound image using the local machine-learning model to generate a set of preset parameter values for the ultrasound imaging system;

generate an ultrasound image using the ultrasound imaging system having the set of preset parameter values;

determine an image quality of the ultrasound image; and modify the local machine-learning model based on the determined image quality.

* * * * *